United States Patent [19]

Shu et al.

[11] Patent Number: 4,568,486

[45] Date of Patent: Feb. 4, 1986

[54] AUGMENTING OR ENHANCING THE LEATHER AROMA OF PERFUME COMPOSITIONS, PERFUMED POLYMERS, COLOGNES AND PERFUMED ARTICLES OF THE DIETHYL ESTER OF 2-ISOPROPYL-3-OXOSUCCINIC ACID

[75] Inventors: Chi-Kuen Shu, Matawan; Cynthia J. Mussinan, Bricktown; Braja D. Mookherjee, Holmdel; Manfred H. Vock, Locust, all of N.J.

[73] Assignee: International Flavors & Fragrances Inc., New York, N.Y.

[21] Appl. No.: 656,655

[22] Filed: Oct. 1, 1984

[51] Int. Cl.[4] .................................................. A61K 7/46

[52] U.S. Cl. ................................ 252/522 R; 252/8.6; 252/8.9; 252/174.11; 252/301.21; 252/522 A; 424/69; 424/70

[58] Field of Search .................... 252/8.6, 8.9, 174.11, 252/522 R, 522 A, 301.21; 424/69, 70

[56] References Cited

U.S. PATENT DOCUMENTS 4,528,124 7/1985 Sturm et al. .................... 252/522 R

OTHER PUBLICATIONS

Arctander, *Perfume and Flavor Chemicals*, vol. II, (1969), Monograph 2867.

CA 99: 139339e, (1983).

JACS 72, 1352–1356, (1950).

Acta Chem. Scand. 5, 485–486, (1951).

*Primary Examiner*—Thomas A. Waltz

*Attorney, Agent, or Firm*—Arthur L. Liberman

[57] ABSTRACT

Described is the use in augmenting or enhancing the leather aroma of perfume compositions, perfumed polymers, colognes and perfumed articles of the diethyl ester of 2-isopropyl-3-oxosuccinic acid having the structure:

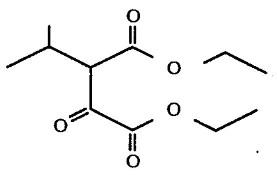

6 Claims, 5 Drawing Figures

GLC PROFILE FOR EXAMPLE I.

NMR SPECTRUM FOR EXAMPLE I.

GC - MS SPECTRUM FOR EXAMPLE I

FIG. 4
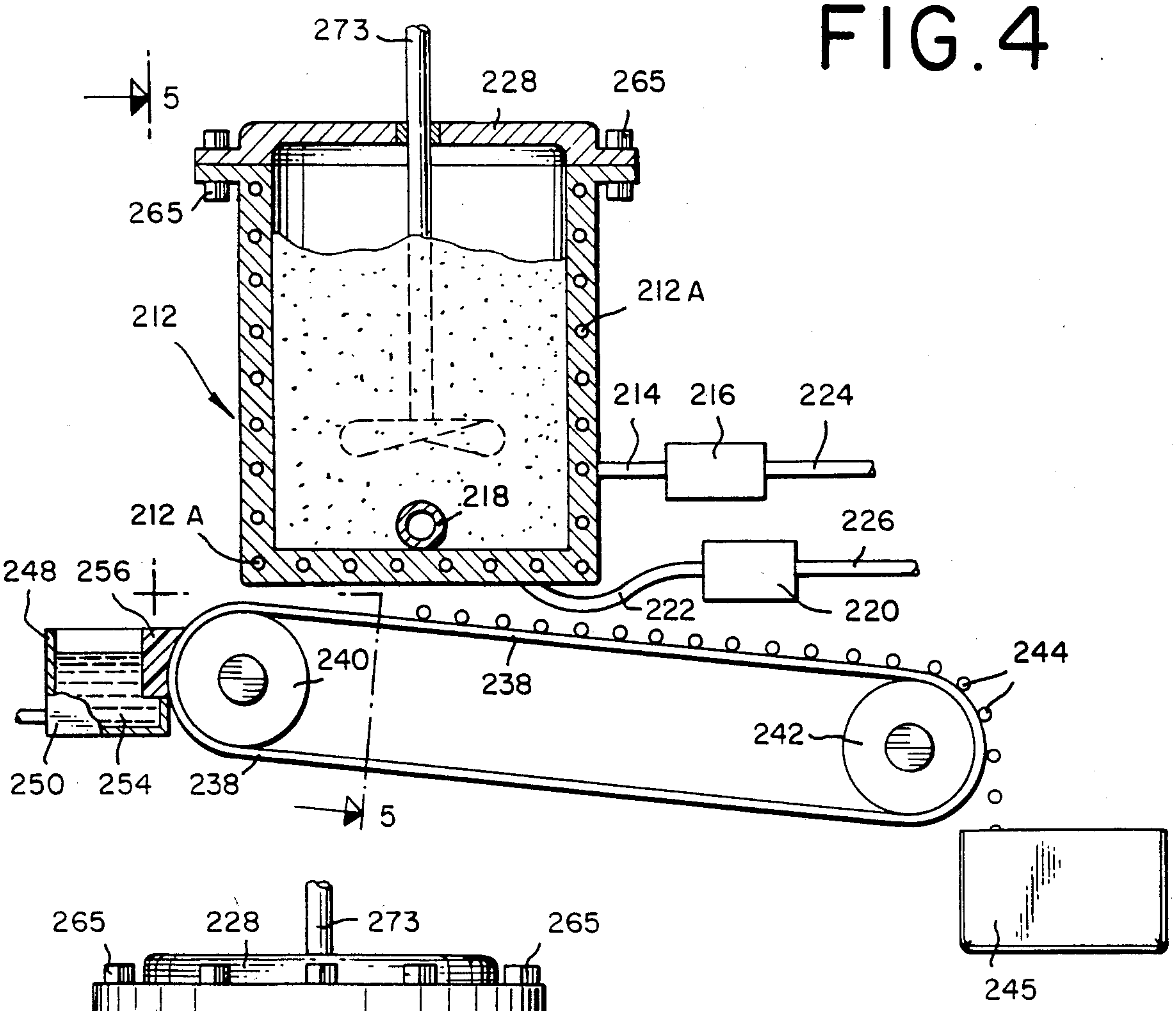
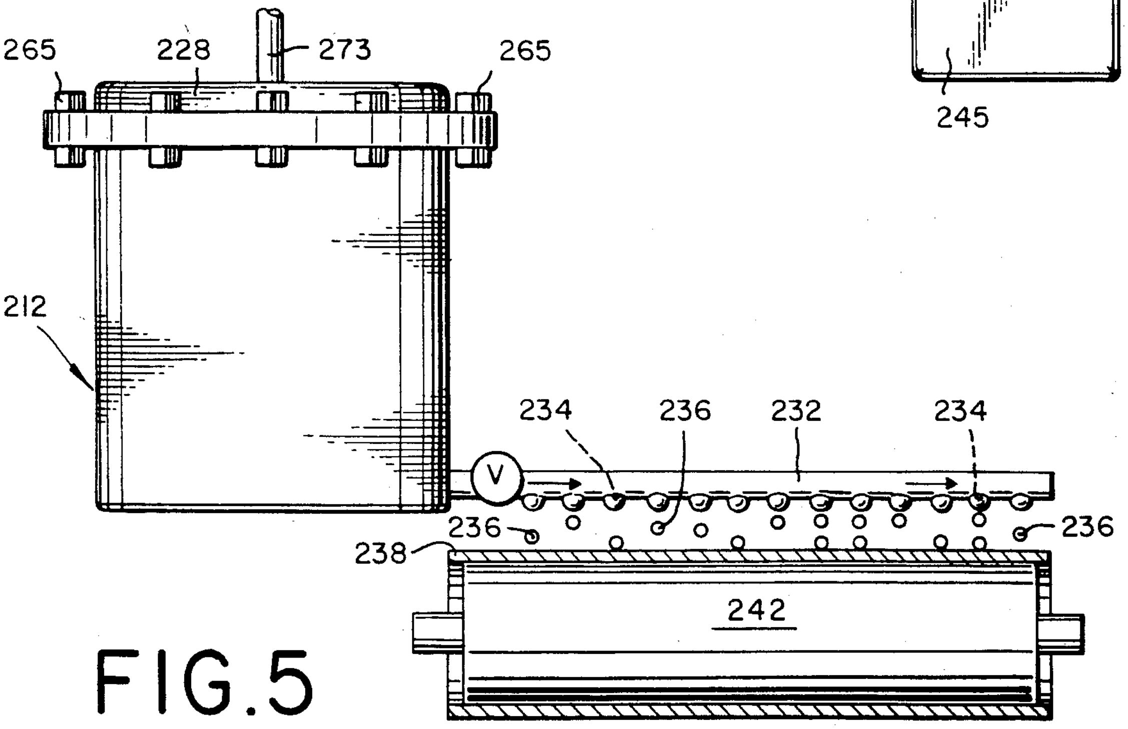
FIG. 5

AUGMENTING OR ENHANCING THE LEATHER AROMA OF PERFUME COMPOSITIONS, PERFUMED POLYMERS, COLOGNES AND PERFUMED ARTICLES OF THE DIETHYL ESTER OF 2-ISOPROPYL-3-OXOSUCCINIC ACID

BACKGROUND OF THE INVENTION

Materials which can provide leathery and castoreum aromas, particularly those materials which are relatively inexpensive, are highly sought after in the art of perfumery. Many of the natural materials which provide such fragrance profiles and contribute desired nuances to perfumery compositions and perfumed article substances are high in cost, vary in quality from one batch to another and/or are generally subject to the usual variations of natural products.

There is, accordingly, a continuing effort to find synthetic materials which will replace the essential fragrance notes provided by the natural essences or compositions thereof. Unfortunately, many of these synthetic materials either have the desired nuances only to a relatively small degree or else contribute undesirable or unwanted odor to the composition. The search for materials which can provide a more refined leathery and castoreum aroma profile has been difficult and relatively costly in the areas of both natural products and synthetic products.

The compound having the structure:

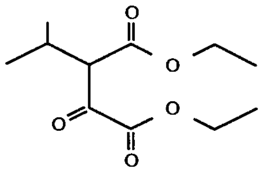

is a known compound disclosed at Chemical Abstracts Volume 99, Monograph 139339e (abstract of Japanese Kokai Tokkyo Koho No. 58/94042; J. Am. Chem. Soc. 72, 1352-6 (1950); and Acta Chem. Scand. 5, 485-6 (1951).

Nothing in the prior art, however, infers or states that the diethyl ester of 2-isopropyl-3-oxosuccinic acid of our invention can be used in augmenting or enhancing leathery aromas or imparting leathery aromas.

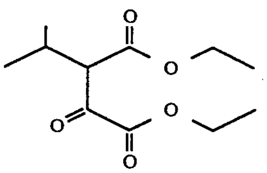

(Conditions: 50M×0.32M carbowax 20M fused silica capillary column programmed at 50°-225° C. at 2° C. per minute).

Figure 2:
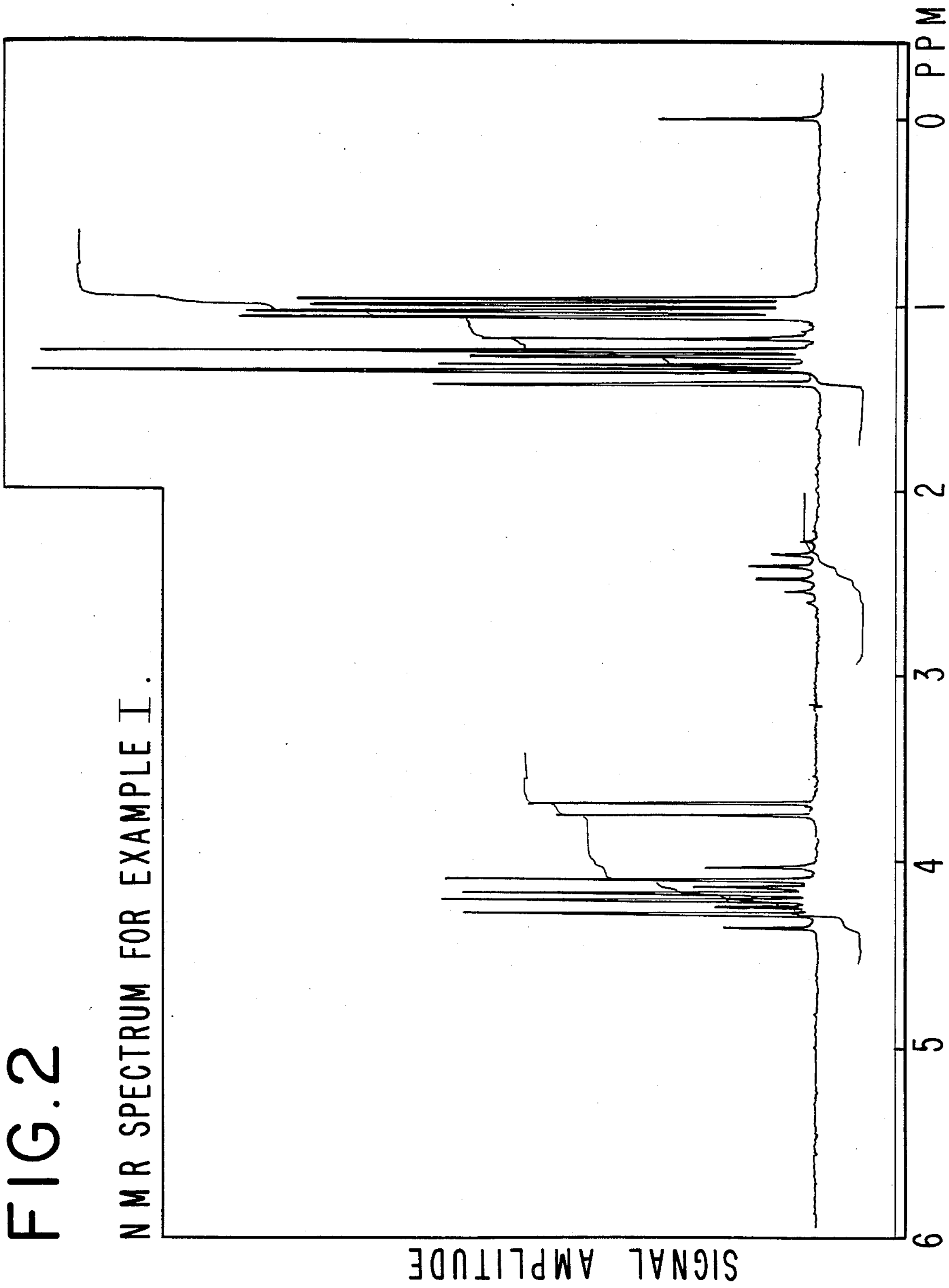

FIG. 2 is the NMR spectrum for the diethyl ester of 2-isopropyl-3-oxosuccinic acid having the structure:

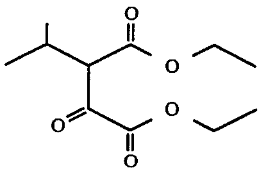

produced according to Example I (Conditions: Field strength: 100 MHz; solvent: $CFCl_3$).

Figure 3:
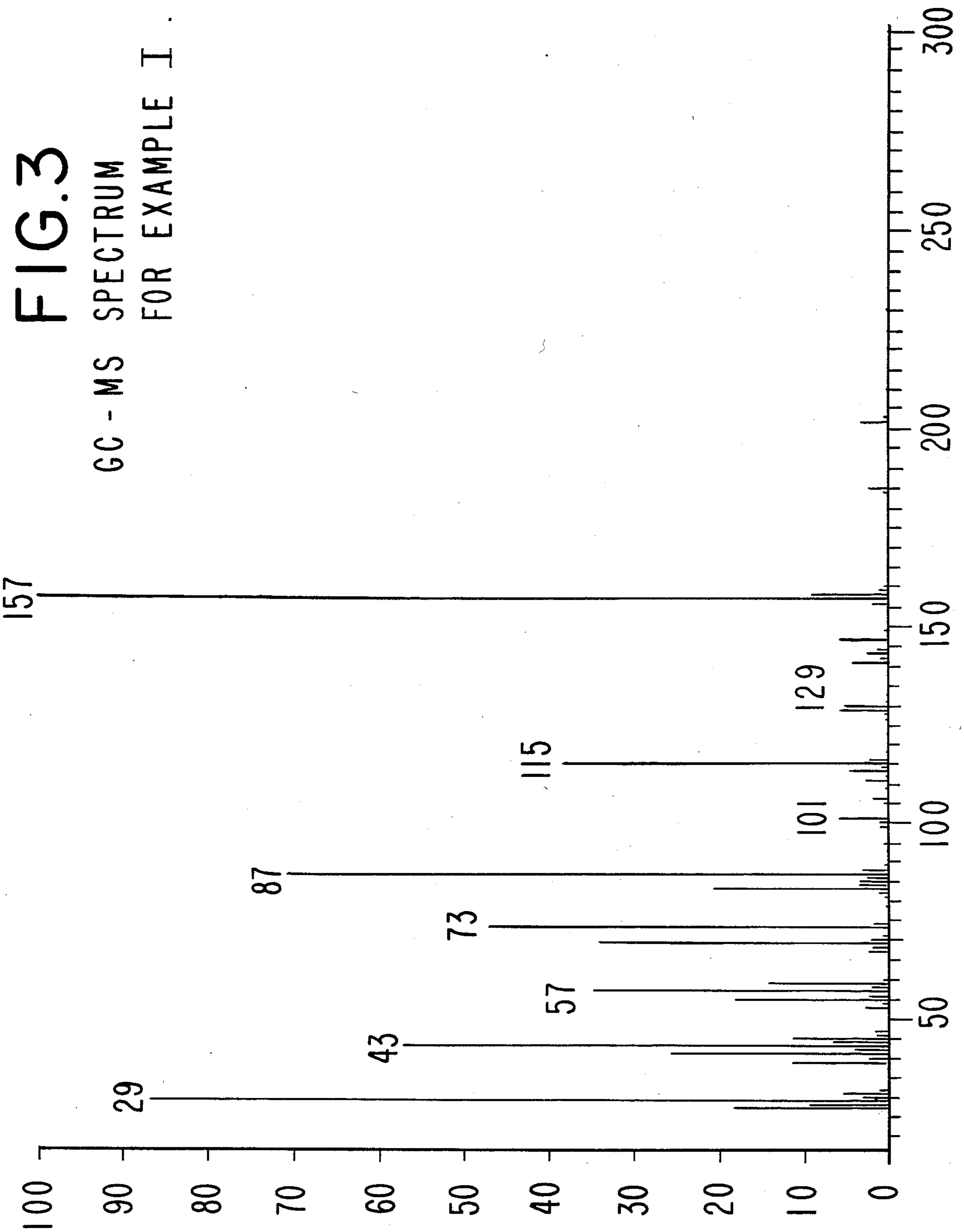

FIG. 3 is the GC-MS spectrum for the compound having the structure:

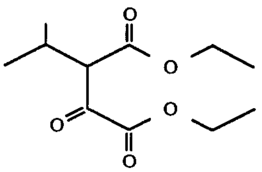

produced according to Example I.

FIG. 4 is a partial side elevation and partial sectional view of an apparatus for forming leather scented polymers using the compound having the structure:

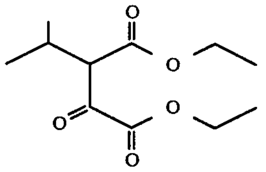

FIG. 5 is a section taken on line 5—5 of FIG. 4.

DETAILED DESCRIPTION OF THE DRAWINGS

Referring to the drawings in FIGS. 4 and 5 in particular, the invention embodied therein comprises a device for forming leather scented polymer pellets (e.g., polyethylene, polypropylene or mixtures of polyepsilon caprolactone and polyethylene or polypropylene or copolymers of polyvinyl acetate and polyethylene or the like) which comprises a vat or container 210 into which a mixture of polymers such as polyethylene and the diethyl ester of 2-isopropyl-3-oxosuccinic acid of our invention having the structure:

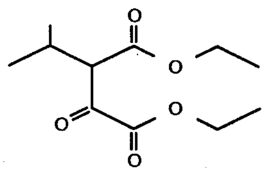

or a mixture of leathery perfume materials including as a key ingredient the diethyl ester of 2-isopropyl-3-oxosuccinic acid of our invention having the structure:

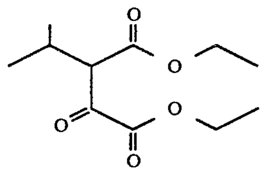

is placed.

The container is closed by an air-tight lid 228 clamped to the container by clamps 265. A stirrer 273 traverses the lid or cover 228 in air-tight manner and is rotated in a suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212 is operated to maintain the upper portion of the container 210 within a temperature range of from 250°-350° F. An additional bottom heater 218 is regulated through control 220 connected thereto through a connecting wire 222 to maintain the lower portion of the container 210 within a temperature range of from 250° to 350° F.

In accordance with this aspect of the invention, a polymer such as polyethylene or polypropylene is added to the container 210 and is then heated from 10 to 12 hours whereafter a leathery scent or aroma imparting material containing the diethyl ester of 2-isopropyl-3-oxosuccinic acid having the structure:

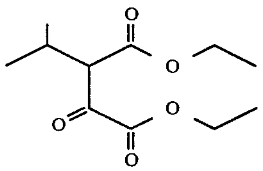

of our invention is quickly added to the melt. The material must be compatible with the polymer and forms a homogeneous liquid melt therewith. The heat resisting mixture generally containing about 5-40% by weight of the diethyl ester of 2-isopropyl-3-oxosuccinic acid of our invention having the structure:

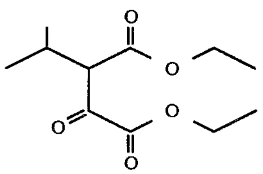

or mixture containing such compound is added to the polymer.

After the diethyl ester of 2-isopropyl-3-oxosuccinic acid of our invention having the structure:

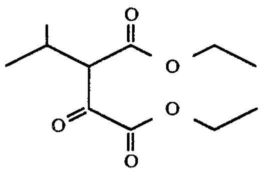

is added to container 210, the mixture is stirred for a few minutes, for example, 5-15 minutes, and maintained within the the temperature range as indicated previously by the heating coils 212 and 218 respectively. The controls 216 and 220 are connected through cables 224 and 226 to a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and substance containing the diethyl ester of 2-isopropyl-3-oxosuccinic acid of out invention having the structure:

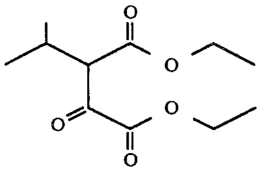

will continuously drop through the orifice 234 downwardly from the conduit 232. During this time the temperature of the polymer and the diethyl ester of 2-isopropyl-3-oxosuccinic acid of our invention having the structure:

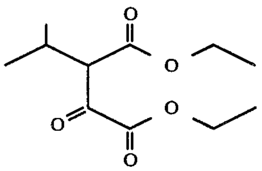

in the container 210 is accurately controlled so that a temperature in the range of from 210 up to 275° F. will be maintained in the material exiting in the conduit 232. The regulation of the temperature through the control 216 and the control 220 is essential in order to insure temperature balance to provide for the continuous dropping or dripping of the molten polymer and the material having the structure:

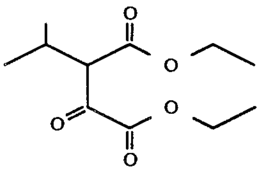

or mixture containing same through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer leather scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

It has now been determined that the diethyl ester of 2-isopropyl-3-oxosuccinic acid having the structure:

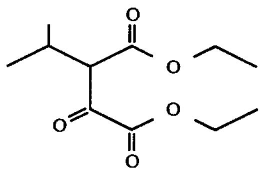

is capable of augmenting, enhancing or imparting leather and castoreum aromas to perfume compositions, perfumed polymers, colognes or perfumed articles, for example, solid or liquid anionic, cationic, nonionic or zwitterionic detergents, fabric softener compositions, fabric softener articles, optical brighteners, hair preparations, cosmetic powders and the like. The diethyl ester of 2-isopropyl-3-oxosuccinic acid of our invention may be prepared by reacting ethyl isovalerate having the structure:

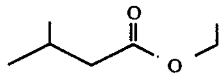

with diethyl oxalate according to the reaction:

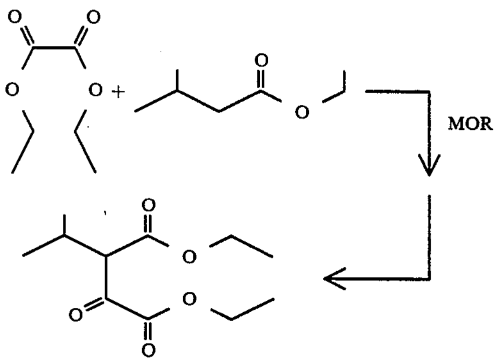

in the presence of an alkali metal alkoxide wherein M represents alkali metal such as sodium and potassium and R represents alkyl such as methyl, ethyl and isopropyl. The diethyl ester of 2-isopropyl-3-oxosuccinic acid of our invention having the structure:

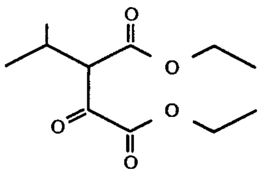

and the method for synthesizing same are well known in the prior art, set forth, supra.

The diethyl ester of 2-isopropyl-3-oxosuccinic acid of our invention can be used to contribute leathery, castoreum aromas to perfume compositions, perfumed polymers such as those disclosed in Letters U.S. Pat. No. 4,465,730 issued on Aug. 14, 1984, the specification for which is incorporated by reference herein, colognes and perfumed articles. As olfactory agents, the diethyl ester of 2-isopropyl-3-oxosuccinic acid of this invention can be formulated into or used as components of a "perfume composition".

The term "perfume composition" is used herein to mean a mixture of organic compounds, including, for example, alcohols, aldehydes, ketones, nitriles, esters other than the ester of this invention, and frequently hydrocarbons which are admixed so that the combined odors of the individual components produce a pleasant or desired fragrance. Such a perfume composition usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, the individual component will contribute its particular olfactory characteristics but the overall effect of the perfume composition will be the sum of the effects of each of the ingredients. Thus, the diethyl ester of 2-isopropyl-3-oxosuccinic acid of this invention can be used to alter the aroma characteristics of a perfume composition, for example, by highlighting or moderating the olfactory reaction contributed by another ingredient in the composition.

The amount of the diethyl ester of 2-isopropyl-3-oxosuccinic acid of this invention which will be effective in perfume compositions depends on many factors including the other ingredients, their amounts and the effects which are desired. It has been found that perfume compositions containing as little as 0.05% and as much as 5% of the diethyl ester of 2-isopropyl-3-oxosuccinic acid of this invention can be used to impart, augment or enhance leathery and castoreum aromas to soaps, cosmetics, solid or liquid anionic, cationic, nonionic or zwitterionic detergents, perfumed polymers, fabric softener compositions, dryer-added fabric softener articles, e.g., BOUNCE® and other products. The amount of employed can range from 1% up to 50% of the fragrance and can be as low as 1% of the original fragrance and will depend on considerations of cost, nature of the end product, the effects desired in the finished product and the particular fragrance sought.

The diethyl ester of 2-isopropyl-3-oxosuccinic acid of this invention can be used alone or in a perfume composition as an olfactory component in detergents and soaps, space odorants and deodorants, perfumes, colognes, toilet waters, bath salts, hair preparations such as lacquers, brilliantines, pomades and shampoos, cosmetic preparations such as creams, deodorants, hand lotions and sun screens, powders such as talcs, dusting powders, face powders and the like. When used as an olfactory component of a perfumed article as little as 0.05% of the diethyl ester of 2-isopropyl-3-oxosuccinic acid of this invention will suffice to impart a leathery, castoreum aroma. Generally, no more than 5.0% is required. Accordingly, the range in the perfumed article of the use of the diethyl ester of 2-isopropyl-3-oxosuccinic of this invention is from about 0.05% up to about 5.0%.

In addition, the perfume composition can contain a vehicle or carrier for the diethyl ester of 2-isopropyl-3-oxosuccinic acid taken alone or taken together with other ingredients. The vehicle can be a liquid such as an alcohol such as ethanol, a glycol such as propylene glycol or the like. The carrier can be an absorbent solid such as a gum or a microporous polymer or components for encapsulating the composition as by means of coacervation (e.g., gelatin or gum arabic or guar gum or xanthan gum).

The following Example I is given to illustrate a technique for producing the diethyl ester of 2-isopropyl-3-oxosuccinic acid of this invention. Examples II and onwards are given to illustrate embodiments of our invention as it is presently preferred to practice it. It will be understood that these examples are illustrative and that the invention is not to be considered restricted thereto except as indicated in the appended claims.

EXAMPLE I

PREPARATION OF DIETHYL ESTER OF 2-ISOPROPYL-3-OXOSUCCINIC ACID

Reaction:

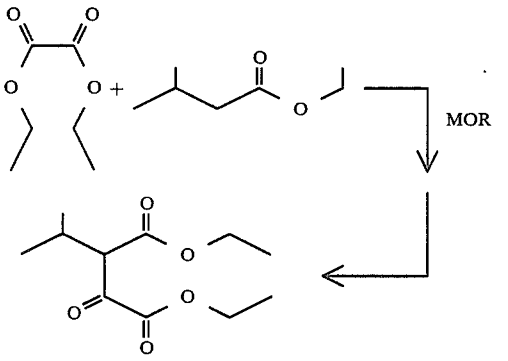

(wherein M represents sodium and R represents ethyl).

Into a 2 liter three necked reaction flask equipped with stirrer, thermometer, condenser, addition funnel and nitrogen inlet tube is placed 800 ml anhydrous toluene and 41 grams of sodium ethoxide. Over a period of 30 minutes from the addition funnel a mixture of 73 grams diethyl oxalate (0.5 moles) and 65 grams of ethyl valerate (0.5 moles) is added to the reaction mass while maintaining the reaction temperature at 35° C. At the end of the addition period, the reaction mass is heated to to 50° C. and maintained at 50° C. with stirring for a period of 10 hours. At the end of the 10 hour period the reaction mass is cooled to room temperature and 300 ml water is added. The pH is adjusted to 6 using 5% aqueous hydrochloric acid (70 ml).

The organic phase is separated from the aqueous phase and the organic phase is washed with 400 ml water and then dried over anhydrous sodium sulphate. The organic phase is then concentrated on a rotary evaporator to 30 grams. The resulting product is distilled at 80° C. and 0.7 mm/hg yielding the diethyl ester of 2-isopropyl-3-oxosuccinic acid having the structure:

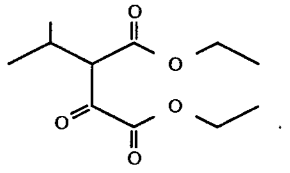

Figure 1:
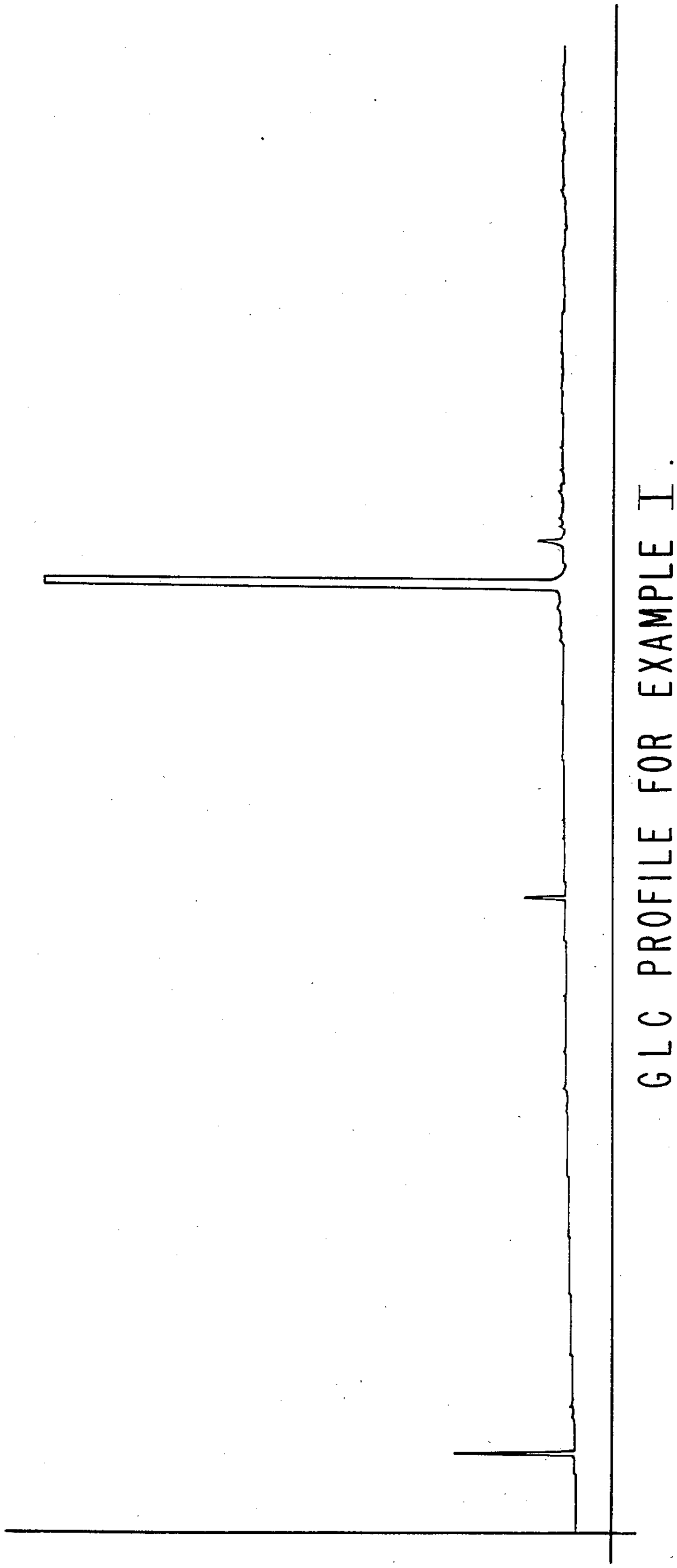
FIG. 1 is the GLC profile for the reaction product of Example I containing the compound having the structure.

FIG. 1 is the GLC profile for the crude reaction product prior to distillation (conditions: 50M×0.32M fused silca capillary column coated with carbowax 20M programmed at 50°–225° C. at 2° C. per minute).

FIG. 2 is the NMR spectrum for the diethyl ester of 2-isopropyl-3-oxosuccinic acid having the structure:

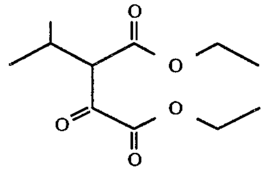

(Conditions: Field strength: 100 MHz; solvent: $CFCl_3$).

FIG. 3 is the GC-MS spectrum for diethyl ester of 2-isopropyl-3-oxosuccinic acid having the structure:

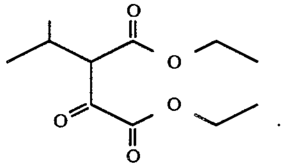

EXAMPLE II

LEATHER FRAGRANCE

The following leather fragrance is prepared:

| INGREDIENTS | WEIGHT PERCENT |
|---|---|
| Diethyl ester of 2-isopropyl-3-oxosuccinic acid having the structure: 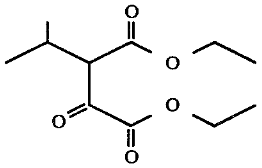 produced according to Example I | 3% |
| Methyl nonyl ketone | 4% |
| 2-undecanol | 4% |
| m-xylene | 6% |
| 2,4-di-n-propyl phenol | 5% |
| Ethyl laurate | 40% |
| n-octane | 19% |

-continued

| INGREDIENTS | WEIGHT PERCENT |
|---|---|
| n-dodecane | 19% |

The resulting perfume composition is compared with a perfume composition identical with the exception that it lacks the diethyl ester of 2-isopropyl-3-oxosuccinic acid having the structure:

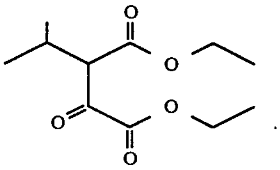

A side-by-side bench panel of five members compared both compositions with and without the diethyl ester of 2-isopropyl-3-oxosuccinic acid having the structure:

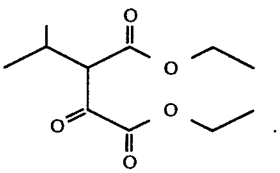

The perfume composition containing the diethyl ester of 2-isopropyl-3-oxosuccinic acid having the structure:

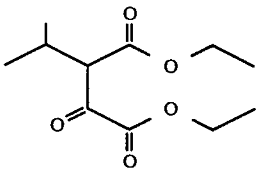

is unanimously preferred by the bench panel as having a more natural-like leathery aroma with excellent natural castoreum nuances.

Accordingly, the perfume composition can be described as: "Leathery aroma with natural leather and castoreum topnotes".

PREPARATION OF A COSMETIC POWDER COMPOSITION

A cosmetic powder is prepared by mixing in a ball mill, 100 grams of talcum powder with 0.25 grams of a composition of matter as set forth in Table I below. Each of the cosmetic powders prepared with each of the ingredients of the composition of matter set forth in Table I below has an aroma as set forth in Table I below:

TABLE I

| PERFUMERY SUBSTANCE | AROMA |
|---|---|
| Compound having the structure: 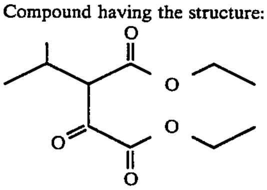 | A leathery, castoreum aroma |
| Perfume composition of Example II | A leathery aroma with natural leather and castoreum topnotes |

EXAMPLE IV

PERFUMED LIQUID DETERGENT

Concentrated liquid detergents (Lysine salt of N-dodecylbenzene sulfonic acid, as more specifically described in Letters U.S. Pat. No. 3,948,818 issued on Apr. 6, 1976) (the specification for which is incorporated by reference herein) with aroma nuances as set forth in Table I of Example III, supra, are prepared containing 0.10%, 0.15% and 0.20% of the fragrance set forth in Table I of Example III, supra. They are prepared by adding and homogeneously mixing the appropriate quantity of fragrance formulation as set forth in Table I of Example III in the liquid detergent. The detergents all possess excellent aromas as set forth in Table I of Example III, the intensity increasing with greater concentrations of perfume composition of Table I of Example III.

EXAMPLE V

PREPARATION OF COLOGNES AND HANDKERCHIEF PERFUMES

Compositions as set forth in Table I of Example III are incorporated into colognes at concentrations of 2.0%, 2.5%, 3.0%, 3.5%, 4.0%, 4.5% and 5.0% in 85%, 90% and 95% aqueous food grade ethanol solutions, and into handkerchief perfumes at concentrations of 15%, 20%, 25% and 30% (in 85%, 90% and 95% aqueous food grade ethanol solutions). Distinctive and definitive aromas as set forth in Table I of Example III are imparted to the cologne and to the handkerchief perfume at all levels indicated above.

EXAMPLE VI

PREPARATION OF SOAP COMPOSITION

One hundred grams of soap chips (IVORY ®, registered trademark of the Proctor and Gamble Co. of Cinncinati, Ohio) are mixed with one gram of each of the perfume substantives of Table I of Example III until a homogeneous composition is obtained. The homogeneous composition is then treated under three atmospheres pressure at 180° C. for a period of three hours and the resulting liquid is placed in soap molds. The resulting soap cake, on cooling, manifests an excellent aroma as set forth in Table I of Example III.

EXAMPLE VII

PREPARATION OF A SOLID DETERGENT COMPOSITION

A detergent is prepared from the following ingredients according to Example I of Canadian Pat. No. 1,007,948 (the specification of which is incorporated by reference herein):

| INGREDIENTS | PERCENT BY WEIGHT |
|---|---|
| "Neodol 45-II" (a $C_{14}$-$C_{15}$ alcohol ethoxylated with 11 moles of ethylene oxide | 12 |

-continued

| INGREDIENTS | PERCENT BY WEIGHT |
|---|---|
| Sodium carbonate | 55 |
| Sodium citrate | 20 |
| Sodium sulfate, water brighteners q.s. | |

The detergent is a "phosphate-free" detergent. A total of 100 grams of this detergent is admixed with 0.15 grams each of the perfume substantives of Table I of Example III. The detergent samples each have aromas as set forth in Table I of Example III.

EXAMPLE VIII

Utilizing the procedure of Example I of column 15 of Letters U.S. Pat. No. 3,632,396 (the specification for which is incorporated by reference herein), a nonwoven cloth of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of each of the perfume substances of Table I of Example III.

A fabric softening composition prepared as set forth above having the above aroma characteristics, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aromas set forth in Table I of Example III are imparted in a pleasant manner to the head space in the dryer-added fabric softening nonwoven fabric.

The disclosure of Letters U.S. Pat. No. 3,632,396 in its entirety is hereby incorporated into the instant patent application. Thus, the fabric softening articles as covered by Letters U.S. Pat. No. 3,632,396 can be incorporated with the perfume compositions of Table I of Example III.

What is claimed is:

1. A process for augmenting or enhancing the leather aroma of a perfume composition, perfumed polymer, cologne or perfumed article comprising the step of adding to a perfume composition, a cologne, a polymer or a perfumed article an aroma augmenting or enhancing quantity of diethyl ester of 2-isopropyl-3-oxosuccinic acid defined according to the structure:

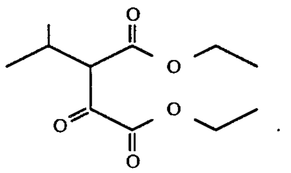

2. The process of claim 1 wherein the diethyl ester of 2-isopropyl-3-oxosuccinic acid is added to a perfume composition.

3. The process of claim 1 wherein the diethyl ester of 2-isopropyl-3-oxosuccinic acid is added to a polymer.

4. The process of claim 1 wherein the diethyl ester of 2-isopropyl-3-oxosuccinic acid is added to a cologne.

5. The process of claim 1 wherein the diethyl ester of 2-isopropyl-3-oxosuccinic acid is added to a perfumed article and the perfumed article is a solid or liquid anionic, cationic, nonionic or zwitterionic detergent.

6. The process of claim 1 wherein the diethyl ester of 2-isopropyl-3-oxosuccinic acid is added to a perfumed article and the perfumed article is a dryer-added fabric softener article or a fabric softener composition.

* * * * *